United States Patent
Inman et al.

(10) Patent No.: US 8,140,159 B2
(45) Date of Patent: Mar. 20, 2012

(54) SAFE-MODE OPERATION OF AN IMPLANTABLE MEDICAL DEVICE

(75) Inventors: Dana Michael Inman, Seabrook, TX (US); Randolph K. Armstrong, Houston, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 476 days.

(21) Appl. No.: 11/186,547

(22) Filed: Jul. 21, 2005

(65) Prior Publication Data

US 2007/0021814 A1  Jan. 25, 2007

(51) Int. Cl.
*A61N 1/18* (2006.01)

(52) U.S. Cl. .......................................... 607/27

(58) Field of Classification Search ................ 607/9, 27; 128/901

See application file for complete search history.

(56) References Cited

U.S. PATENT DOCUMENTS

| | | | |
|---|---|---|---|
| 4,091,818 A * | 5/1978 | Brownlee et al. | 607/9 |
| 4,745,923 A | 5/1988 | Winstrom | |
| 5,217,010 A | 6/1993 | Tsitlik et al. | |
| 5,647,379 A * | 7/1997 | Meltzer | 128/897 |
| 6,198,972 B1 * | 3/2001 | Hartlaub et al. | 607/63 |
| 6,317,633 B1 | 11/2001 | Jorgenson et al. | |
| 6,591,139 B2 | 7/2003 | Loftin et al. | |
| 6,711,440 B2 | 3/2004 | Deal et al. | |
| 6,718,203 B2 | 4/2004 | Weiner et al. | |
| 6,718,207 B2 | 4/2004 | Connelly | |
| 6,725,092 B2 | 4/2004 | MacDonald et al. | |
| 6,731,979 B2 | 5/2004 | MacDonald | |
| 6,757,566 B2 | 6/2004 | Weiner et al. | |
| 6,760,628 B2 | 7/2004 | Weiner et al. | |
| 6,763,268 B2 | 7/2004 | MacDonald et al. | |
| 6,778,856 B2 | 8/2004 | Connelly et al. | |
| 6,788,972 B2 * | 9/2004 | Prutchi et al. | 607/28 |
| 6,795,730 B2 | 9/2004 | Connelly et al. | |
| 6,795,736 B2 | 9/2004 | Connelly et al. | |
| 6,799,069 B2 | 9/2004 | Weiner et al. | |
| 6,819,954 B2 | 11/2004 | Connelly | |
| 6,819,958 B2 | 11/2004 | Weiner et al. | |
| 6,829,509 B1 | 12/2004 | MacDonald et al. | |
| 6,845,266 B2 | 1/2005 | Weiner et al. | |

(Continued)

FOREIGN PATENT DOCUMENTS

EP  0713714  5/1996

(Continued)

OTHER PUBLICATIONS

Bohning, D.E. et al., "Feasibility of Vagus Nerve Stimulation-Synchronized Blood Oxygenation Level-Dependent Functional MRI," Investigative Radiology, vol. 36, No. 8, (Aug. 2001), pp. 470-479.

(Continued)

*Primary Examiner* — Scott Getzow
*Assistant Examiner* — Amanda Patton
(74) *Attorney, Agent, or Firm* — Williams, Morgan & Amerson, P.C.; Jonathan D. Rowell; Darrell N. Fuller

(57) ABSTRACT

A method, system, and apparatus for implementing a safe mode operation of an implantable medical system using impedance adjustment(s) are provided. A first impedance is provided to a lead. An indication of a possibility of a coupled energy is received. Based upon said indication, a second impedance associated with the lead to reduce the coupled energy is provided.

25 Claims, 9 Drawing Sheets

U.S. PATENT DOCUMENTS

| | | |
|---|---|---|
| 6,850,805 B2 | 2/2005 | Connelly et al. |
| 6,875,180 B2 | 4/2005 | Weiner et al. |
| 6,901,290 B2 | 5/2005 | Foster et al. |
| 6,901,292 B2 * | 5/2005 | Hrdlicka et al. ............. 607/27 |
| 6,925,328 B2 | 8/2005 | Foster et al. |
| 6,949,929 B2 | 9/2005 | Gray et al. |
| 6,954,674 B2 | 10/2005 | Connelly |
| 6,985,775 B2 | 1/2006 | Reinke et al. |
| 6,988,001 B2 | 1/2006 | Greatbatch et al. |
| 6,993,387 B2 | 1/2006 | Connelly et al. |
| 7,010,357 B2 | 3/2006 | Helfer et al. |
| 7,013,174 B2 | 3/2006 | Helfer et al. |
| 7,015,393 B2 | 3/2006 | Weiner et al. |
| 7,047,074 B2 | 5/2006 | Connelly et al. |
| 7,054,686 B2 | 5/2006 | MacDonald |
| 7,123,013 B2 | 10/2006 | Gray |
| 2002/0133204 A1 | 9/2002 | Hrdlicka |
| 2003/0140931 A1 * | 7/2003 | Zeijlemaker et al. ......... 128/899 |
| 2004/0263172 A1 | 12/2004 | Gray et al. |
| 2005/0143786 A1 | 6/2005 | Boveja et al. |

FOREIGN PATENT DOCUMENTS

| | | |
|---|---|---|
| WO | 2004036377 A2 | 4/2004 |

OTHER PUBLICATIONS

Devous, Michael, et al., "Effects of Vagus Nerve Stimulation on Regional Cerebral Blood Flow in Treatment-Resistant Depression," National Institute of Mental Health, 42nd annual New Clinical Drug Evaluation Unit Meeting: Poster Session II, Poster Abstracts, Jun. 10-13, 2002, 1 page.

Koo, Betty, "EEG Changes With Vagus Nerve Stimulation," Journal of Clinical Neurophysiology, vol. 18, No. 5, (Sep. 2001), pp. 434-441.

Terry, R.S., et al., "The Implantable Neurocybernetic Prosthesis System," Pacing and Clinical Electrophysiology, vol. 14, No. 1, (Jan. 1991), pp. 86-93.

Zabara, J., et al., "Inhibition of Experimental Seizures in Canines by Repetitive Vagal Stimulation," Epilepsia, 33(6), (1992), pp. 1005-1012.

* cited by examiner

SAFE-MODE OPERATION OF AN IMPLANTABLE MEDICAL DEVICE

CROSS-REFERENCE TO RELATED APPLICATION

This application is a related application to U.S. patent application Ser. No. 11/186,261, entitled "Safe-Mode Implantable Medical Devices," which is filed on the same date as the present application and in the name of the same inventors.

BACKGROUND OF THE INVENTION

1. Field of the Invention

This invention relates generally to implantable medical devices, and, more particularly, to methods, apparatus, and systems for providing a safe-mode operation of the implantable medical device using a dynamic impedance adjustment process.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated in its entirety herein by reference in this specification. Electrical stimulation of the vagus nerve (hereinafter referred to as vagus nerve stimulation therapy or VNS) may be provided by implanting an electrical device underneath the skin of a patient and performing a detection and electrical stimulation process. Alternatively, the system may operate without a detection system once the patient has been diagnosed with epilepsy, and may periodically apply a series of electrical pulses to the vagus (or other cranial) nerve intermittently throughout the day, or over another predetermined time interval.

Generally, therapeutic electrical stimulation is delivered by the implantable device via a lead. The lead generally terminates onto an electrode, which may be affixed onto a tissue. A plurality of electrodes that are associated with an implantable medical device are generally operatively connected to the implantable device via individual leads. Therefore, a number of leads may project from the implantable device onto various portions of a patient's body. For example, a number of electrodes may be attached to various points of a nerve or other tissue inside a human body.

Occasionally, a patient having an implantable device may be subjected to an electrical field, a magnetic field, and/or an electromagnetic field. In the proximity of one of the aforementioned fields, coupled signal and/or noise may appear on various portions of the implantable device system, particularly on the leads. Depending on the strength of the field, a significant amount of coupled energy may appear on the leads. This coupled energy may cause adverse effects. For example, the coupled energy on the leads may affect operation of the device, or cause adverse thermal changes. The coupled signal or energy may also interfere with the delivery of the electrical/magnetic stimulation therapy, or with the proper detection of various signals from the electrodes. Other adverse effects, such as heating of various portions of the implantable system may occur. This heating may damage tissue that is proximate to the portion of the implantable system that experiences thermal the changes.

The present invention is directed to overcoming, or at least reducing, the effects of one or more of the problems set forth above.

SUMMARY OF THE INVENTION

In one aspect, the present invention comprises a method for implementing a safe mode operation of a medical device using impedance adjustment(s). A first impedance is provided to a lead. An indication of a possibility of a coupled energy is received. Based upon said indication, a second impedance associated with the lead to reduce the coupled energy is provided.

In another aspect, the method comprises a method for implementing a safe mode operation of a medical device using impedance adjustment(s). A first impedance associated with a lead set of the implantable medical device for performing the stimulation is provided. A coupled energy on the lead set is detected. A second impedance associated with the lead set in response to detecting the coupled energy is provided.

In a further aspect, an additional method of implementing a safe mode operation using impedance adjustment(s) is provided. Data indicating a potential presence of a field is received. The field is an electrical field, a magnetic field, or an electromagnetic field. An impedance associated with a lead coupled to the IMD is modified based upon the data indicating the potential presence of a field.

In another aspect of the present invention, an implantable medical device is provided implementing a safe mode operation using impedance adjustment(s). The implantable medical device includes a stimulation unit to provide a stimulation signal through a lead operatively coupled to the IMD. The implantable medical device also includes a controller to receive an indication of a possibility of a coupled energy. The controller is also adapted to modify an impedance of the lead set based upon detection of the coupled energy.

In another aspect of the present invention, a medical device system is provided for implementing a safe mode operation using impedance adjustment(s). The system includes an electrode coupled to a tissue in a patient's body, and a lead operatively coupled to the electrode. The lead is adapted to carry a stimulation signal to the electrode. The system includes an implantable medical device (IMD) operatively coupled to the lead. The IMD, which may comprise a signal generator, is adapted to provide a stimulation signal to the tissue through the lead. The IMD includes a stimulation unit to provide a stimulation signal through the lead and a controller to receive an indication of a possibility of a coupled energy. The controller is adapted to also modify an impedance of the lead set based upon the indication of a possibility of a coupled energy.

In yet another aspect, the present invention comprises a computer readable program storage device encoded with instructions for implementing a safe mode operation using impedance adjustment(s). The instructions in the computer readable program storage device, when executed by a computer, perform a method comprising: providing a first impedance relating to the lead; receiving an indication of a possibility of a coupled energy; determining a second impedance associated with the lead to reduce the coupled energy; and modifying the first impedance of the lead to the second impedance.

In another aspect of the present invention, a medical device system is provided for implementing a safe mode operation using impedance adjustment(s). The system includes an electrode coupled to a portion of a tissue in a patient's body. The system also includes a lead operatively coupled to the electrode. The lead is adapted to carry a stimulation signal to the electrode. The system also includes an implantable medical device (IMD) operatively coupled to the lead. The IMD, which may comprise a signal generator, is adapted to provide a stimulation signal to the tissue through the lead. The IMD includes a stimulation unit to provide a stimulation signal through the lead. The IMD further comprises an impedance unit to modify an impedance of the lead based upon a command from an external source. The IMD may optionally comprise a signal detection unit to detect a coupled energy.

BRIEF DESCRIPTION OF THE DRAWINGS

The invention may be understood by reference to the following description taken in conjunction with the accompanying drawings, in which like reference numerals identify like elements, and in which.

Figure 1A:
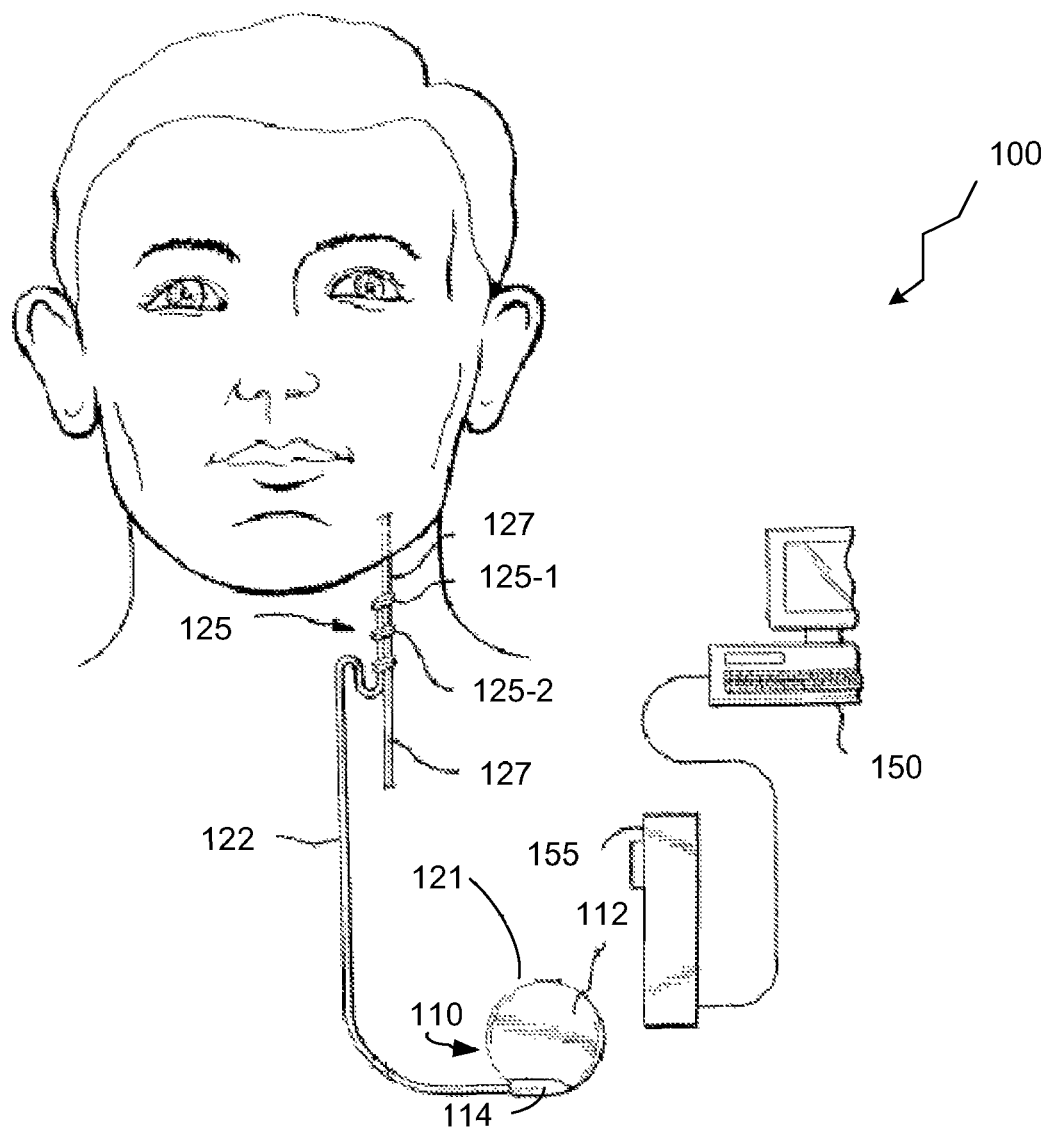
FIGS. 1A-1D provide stylized diagrams of an implantable medical device implanted into a patient's body for providing stimulation to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

FIGS. 1A-1D illustrate an implantable medical system 100 that is capable of entering a safe-mode operation in response to a presence of a coupled signal/energy experienced by a component of the system 100. The safe-mode operation may involve adjusting an impedance associated with the portion of the implantable medical system 100 that is experiencing the presence of the coupled signal/energy. The system 100 is also capable of detecting when the coupled signal/energy has been removed or substantially reduced, and returning to a normal operating mode.

FIGS. 1A-1D depict a stylized implantable medical system 100 for implementing one or more embodiments of the present invention. FIGS. 1A-1D illustrate a signal generator 110 having main body 112 comprising a case or shell 121 with an electrical connector 116 in a header 114 (FIG. 1C) for connecting to leads 122. The signal generator 110 is implanted in the patient's chest in a pocket or cavity formed by the implanting surgeon just below the skin (indicated by a dotted line 145, FIG. 1B), similar to the implantation procedure for a pacemaker pulse generator.

A stimulating electrode assembly 125, preferably comprising an electrode pair, is conductively connected to the distal end of an insulated electrically conductive lead assembly 122, which preferably comprises a pair of lead wires (one wire for each electrode of an electrode pair). Lead assembly 122 is attached at its proximal end to the electrical connector 116 on header 114. The electrode assembly 125 is surgically coupled to the patient's tissue, e.g., a vagus nerve 127 in the patient's neck. The present invention is suitable for use in implantable medical devices connected to any body tissue, e.g., a pacemaker coupled to heart tissue. The electrode assembly 125 preferably comprises a bipolar stimulating electrode pair (FIG. 1D), such as the electrode pair described in U.S. Pat. No. 4,573,481 issued Mar. 4, 1986 to Bullara. Persons of skill in the art will appreciate that many electrode designs could be used in the present invention. For embodiments of the present invention involving vagus nerve stimulation, two electrodes are preferably wrapped about the vagus nerve, and the electrode assembly 125 is preferably secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue.

In one embodiment of the invention involving nerve stimulation, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The elastomeric body portion of each loop preferably comprises silicone rubber, and the third loop 128 (which typically has no electrode) acts as the anchoring tether 128 for the electrode assembly 125.

The lead assembly 122 may comprise two distinct lead wires or a coaxial cable whose two conductive elements are respectively coupled to one of the conductive electrode ribbons 125-1 and 125-2. One suitable method of coupling the lead wires or cable to the electrodes comprises a spacer assembly such as that disclosed in U.S. Pat. No. 5,531,778, although other known coupling techniques may be used.

Figure 1B:
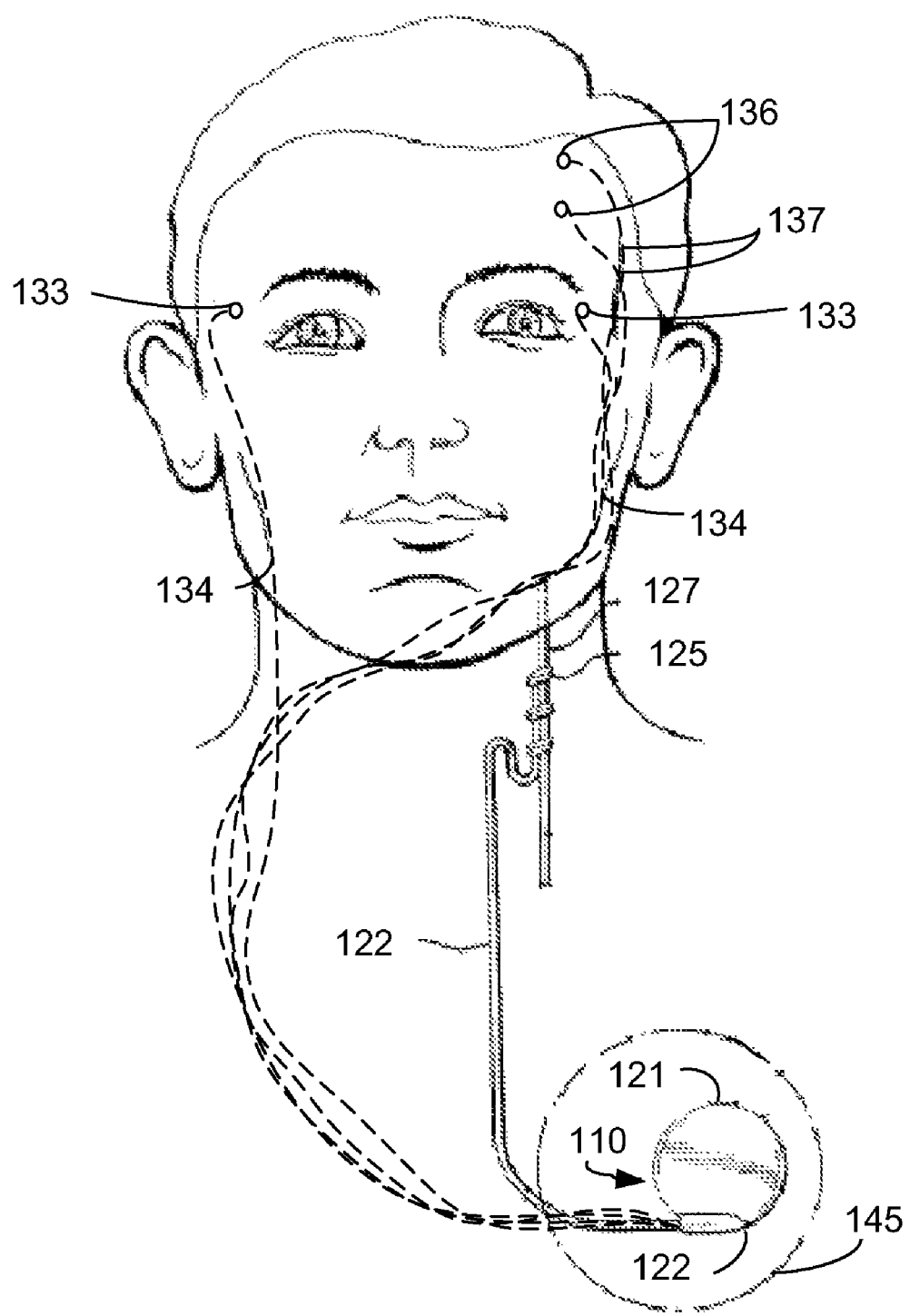
Figure 1C:
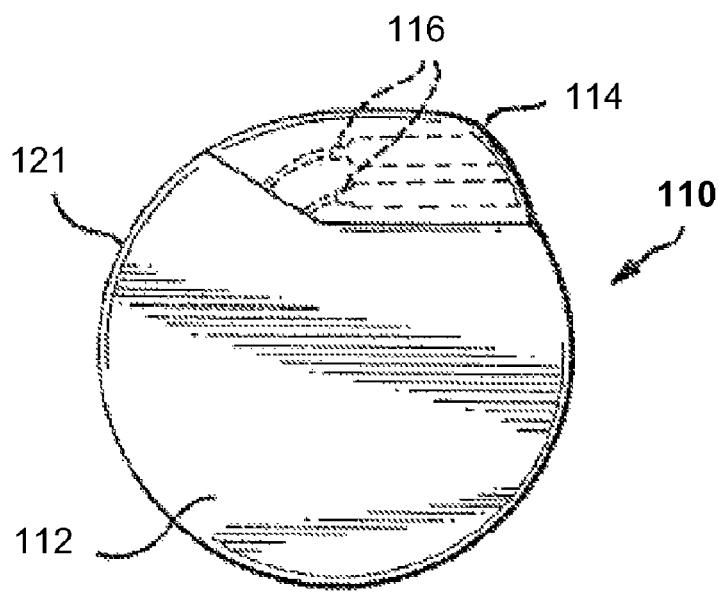
Figure 1D:
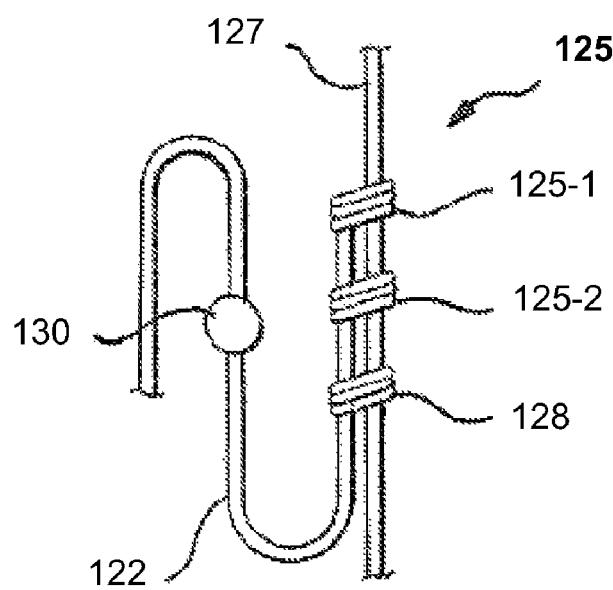

In certain embodiments of the invention, sensing elements may be used to provide data to the implantable medical system 100 concerning one or more body parameters. Although exemplary sensors are disclosed herein, persons of skill in the art will appreciate that the present invention is not limited to particular embodiments. Referring to FIG. 1B, eye movement sensing electrodes 133 may be implanted at or near an outer periphery of each eye socket in a suitable location to sense muscle movement or actual eye movement. The electrodes 133 may be electrically connected to leads 134 implanted via a catheter or other suitable means (not shown) and extending along the jawline through the neck and chest tissue to the signal generator 110. When included in systems of the present invention, the sensing electrodes 133 may be utilized for detecting rapid eye movement (REM) in a pattern indicative of a disorder to be treated, as described in greater detail below.

Alternatively or additionally, EEG sensing electrodes 136 may optionally be implanted in spaced apart relation through the skull, and connected to leads 137 implanted and extending along the scalp and temple and then to the signal generator 110 in the same manner as described above for the eye movement electrode leads. Electrodes 133 and 136, or other types of sensors, may be used in some embodiments of the invention to trigger administration of the electrical stimulation therapy to the vagus nerve 127 via electrode assembly 125. Use of such sensed body signals to trigger or initiate stimulation therapy is hereinafter referred to as a "feedback" or "active" stimulation. Other embodiments of the present invention utilize a stimulation therapy delivered according to a programmed on/off duty cycle without the use of sensors to trigger therapy delivery. This type of delivery may be referred to as "passive," "non-feedback," or prophylactic stimulation. Both active and passive stimulation may be combined or delivered by a single IMD according to the present invention. Either or both modes may be appropriate to treat the particular disorder diagnosed in the case of a specific patient under observation. The therapeutic electrical signal may be a continuous or pulsed signal; either type of signal may be applied periodically or intermittently to the vagus nerve.

The signal generator 110 may be programmed with an external computer 150 (FIG. 1A) using programming software of the type copyrighted by the assignee of the instant application with the Register of Copyrights, Library of Congress, or other suitable software based on the description herein, and a programming wand 155 may be used to facilitate radio frequency (RF) communication between the computer 150 and the signal generator 110. The wand 155 and software permit noninvasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

A wide variety of stimulation therapies may be provided in implantable medical systems 100 of the present invention. Different types of nerve fibers (e.g., A, B, and C fibers being different fibers being targeted for stimulation) respond differently to stimulation from electrical signals. More specifically, the different types of nerve fibers have different conduction velocities and stimulation thresholds, and therefore differ in their responsiveness to stimulation. Certain pulses of an electrical stimulation signal, for example, may be below the stimulation threshold for a particular fiber and therefore may generate no action potential in the fiber. Thus, smaller or narrower pulses may be used to avoid stimulation of certain nerve fibers (such as C fibers) and target other nerve fibers (such as A and/or B fibers, which generally have lower stimulation thresholds and higher conduction velocities than C fibers). Additionally, techniques such as pre-polarization may be employed wherein particular nerve regions may be polarized before a more robust stimulation is delivered, which may better accommodate particular electrode materials. Furthermore, opposing polarity phases separated by a zero current phase may be used to excite particular axons or postpone nerve fatigue during long-term stimulation.

Regardless of the type of stimulation employed, in preferred embodiments of the present invention, the signal generator 110 is coupled to the stimulation electrodes by leads 122. In the presence of a significant electromagnetic field, a coupled signal or energy may appear on these leads. The leads may behave as antennas that initiate an energy gradient on its surface. This energy may interfere with operation of the implantable medical system, and may also cause release of thermal energy, leading to excessive heating of the surrounding tissue. Embodiments of the present invention provide for performing a dynamic adjustment of an impedance to reduce the effects of the coupled signal/energy.

Embodiments of the present invention provide for reducing a coupled signal/energy experienced by a portion (e.g., the leads) of an implantable medical system 100. When a patient experiences an electromagnetic (or any type) of energy field, a coupled energy may appear on a portion of an implantable system. For example, the leads associated with the device may experience a coupled energy that may interfere with various operations of the system 100. The coupled energy may interfere with delivery of stimulation signals provided by the implantable system 100. The coupled energy may also interfere with detection of a signal associated with a patient's body sensed by the implantable device.

Additionally, the energy coupled onto the leads may cause a rise in, or a release of, thermal energy, which may burn or otherwise adversely affect a portion of adjacent tissue. Embodiments of the present invention provide for reducing the coupled energy, thereby preventing or reducing an unwarranted increase in thermal energy. For example, embodiments of the present invention provide for reducing the amount of energy that is coupled onto a portion (e.g., leads) of the implantable system.

An impedance associated with various portions of the implantable system may be modified to substantially reduce energy that is coupled onto a portion of the implantable system 100. For example, if a lead experiences coupled energy, an impedance associated with that particular lead may be adjusted in an automated and/or in a manual fashion. This adjustment of the impedance may cause an attenuation of the coupled energy. Therefore, the impedance between multiple electrodes, the impedance between an electrode and the casing of the device, and/or the impedance between any two points associated with the implantable system 100 may be adjusted or modified according to the type of energy coupled to the medical system 100. Hence, based on the strength, frequency, and/or other characteristics of the coupled energy, one of a plurality of impedance adjustments may be performed to substantially reduce the coupled energy and/or its effects.

Figure 2:
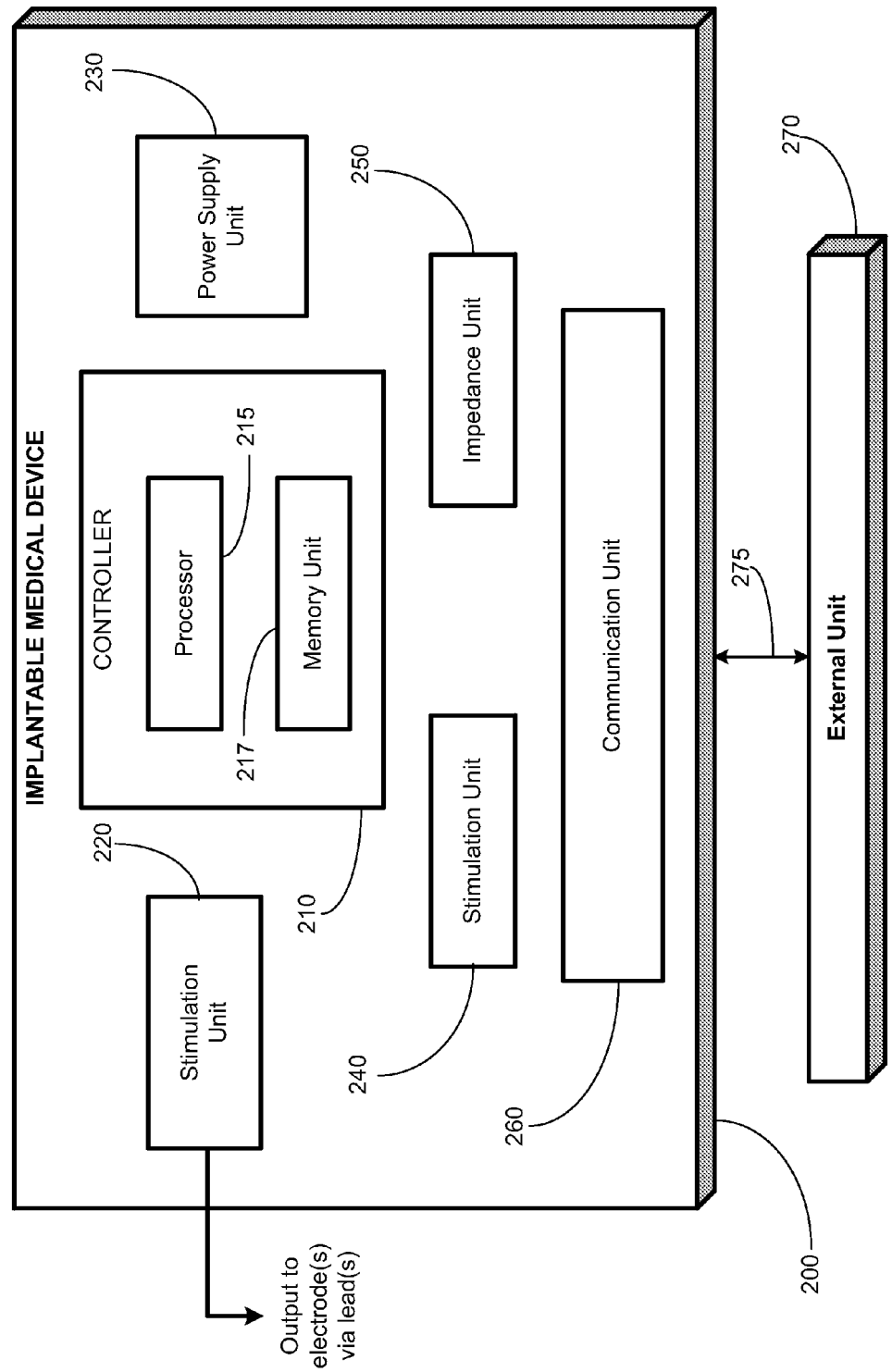
FIG. 2 is a block diagram of an implantable medical device and an external unit that communicates with the implantable medical device, in accordance with one illustrative embodiment of the present invention.

Turning now to FIG. 2, a block diagram depiction of an implantable medical device (IMD), in accordance with one illustrative embodiment of the present invention is illustrated. The IMD 200 may be used for stimulation to treat various disorders, such as epilepsy, depression, bulimia, heart rhythm disorders, etc. The IMD 200 may be coupled to various leads associated with the leads 122 (FIG. 1A). Stimulation signals used for therapy may be transmitted from the IMD 200 to target areas of the patient's body, specifically to various electrodes associated with the leads 122. Stimulation signals from the IMD 200 may be transmitted via the leads 122 to stimulation electrodes associated with the electrode assembly 125 (FIG. 1A). Further, signals from sensor electrodes, e.g., 133, 136 (FIG. 1B) associated with corresponding leads, e.g., 134, 137, may also traverse the leads back to the IMD 200.

The implantable medical device 200 may comprise a controller 210 capable of controlling various aspects of the operation of the IMD 200. The controller 210 is capable of receiving internal data and/or external data and generating and delivering a stimulation signal to target tissues of the patient's body. For example, the controller 210 may receive manual instructions from an operator externally, or may perform stimulation based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., that are capable of performing various executions of software components. The memory 217 may comprise various memory portions where a number of types of data (e.g., internal data, external data instructions, software codes, status data, diagnostic data, etc.) may be stored. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering stimulation signals to one or more electrodes via leads. A number of leads 122, 134, 137 may be coupled to the IMD 200. Therapy may be delivered to the leads 122 by the stimulation unit 220 based upon instructions from the controller 210. The stimulation unit 220 may comprise various circuitry, such as stimulation signal generators, impedance control circuitry to control the impedance "seen" by the leads, and other circuitry that receives instructions relating to the type of stimulation to be performed. The stimulation unit 220 is capable of delivering a controlled current stimulation signal over the leads 122.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230, may comprise a lithium/thionyl chloride cell or a lithium/carbon monofluoride cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 is a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

The IMD 200 also comprises an impedance unit 250 and may optionally comprise a signal detection unit 240. The signal detection unit 240, if present, provides for detecting the presence of a signal/energy. Those skilled in the art would appreciate that concepts of embodiments of the present invention may be implemented without the use of the signal detection unit 240. The signal detection unit 240 is capable of detecting a signal/energy that may be coupled onto any portion of the implantable system 100 (e.g., the electrodes, the leads, and/or the IMD 200). For example, a coupled energy, signal, and/or noise that are coupled onto a lead associated with the IMD 200 may be detected by the signal detection unit 240. A more detailed description of the signal detection unit 240 is provided in FIG. 3 and the accompanying description below.

The impedance unit 250 is capable of modifying the impedance relating to one or more portions of the implantable system. For example, the impedance unit 250 may modify the impedance between one lead relative to another, and/or the impedance between a lead relative to a node associated with the IMD 200. A more detailed description of the impedance unit 250 is provided in FIG. 5 and the accompanying description below.

One or more blocks illustrated in the block diagram of IMD 200 in FIG. 2 may comprise hardware units, software units, firmware units and/or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
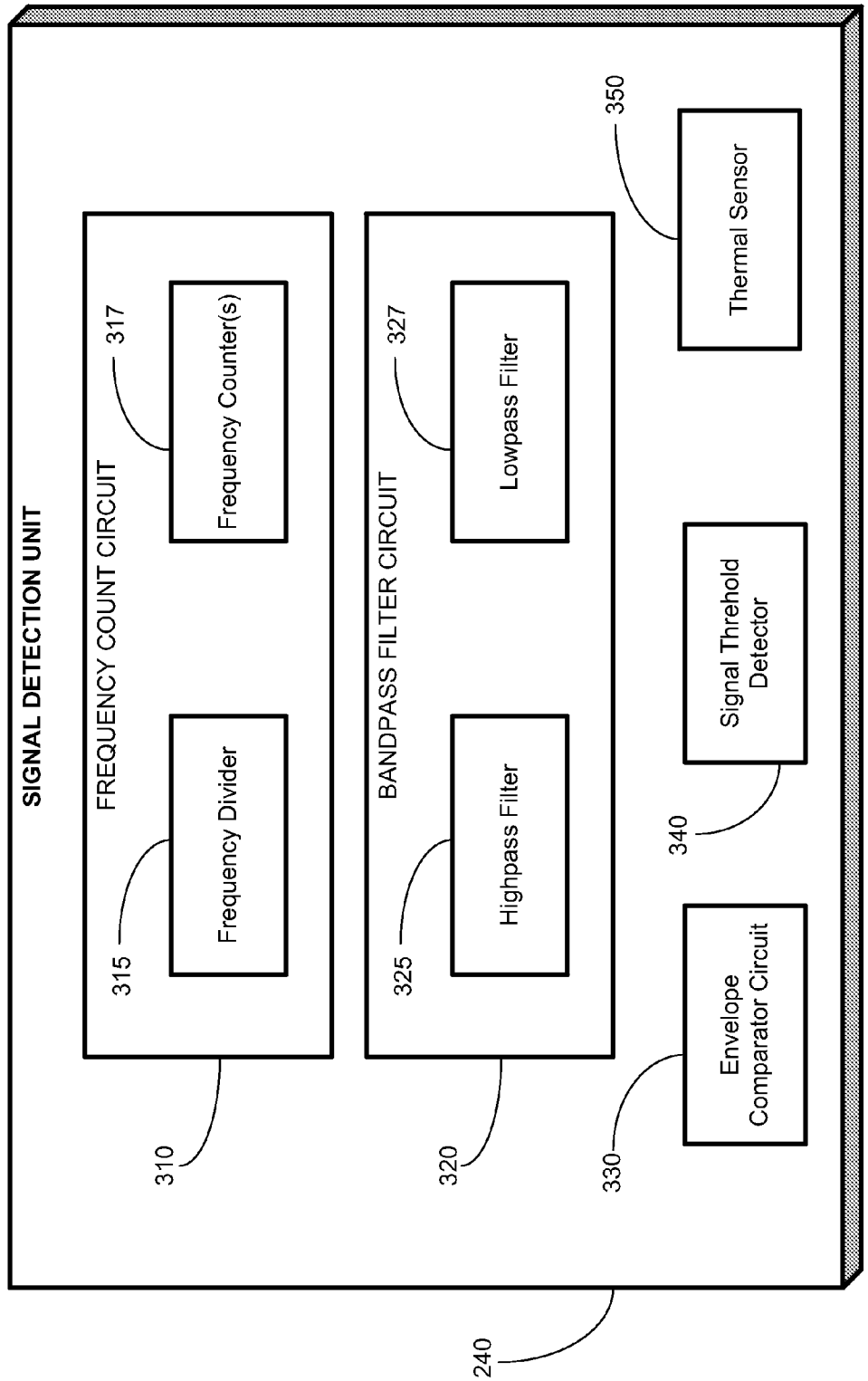
FIG. 3 is a more detailed block diagram depiction of a signal detection unit of the implantable medical device of FIG. 2, in accordance with one illustrative embodiment of the present invention.

Turning now to FIG. 3, a more detailed block diagram illustration of the signal detection unit 240 is provided. A number of methods may be used by those skilled in the art having benefit of the present disclosure to detect a signal, energy, and/or noise that is coupled onto any portion of the implantable system 100. FIG. 3 illustrates exemplary systems to detect such coupled energy. However, those skilled in the art having benefit of the present disclosure would appreciate that a variety of circuits may be used to detect coupled energy, and remain within the spirit and scope of the present invention.

The signal detection unit 240 may comprise a frequency count unit 310. The frequency count unit 310 may comprise various circuit portions, such as a frequency divider 315 and/or a frequency counter 317. The frequency count unit 310 may be capable of detecting a particular type of coupled signal/energy that is coupled onto a portion of the implantable system 100. The frequency count unit 310 is also capable of dividing the frequency and/or counting the number of periods associated with the frequency of the coupled signal/energy. Data relating to the frequency division process and/or the frequency counting process may be used to perform comparison(s) with stored data. This comparison may be useful in determining whether coupled energy rises to the level of requiring an affirmative response by the IMD 200. In other words, the comparison may be used to determine whether an adjustment of the impedance relating to the portion of the IMD 200 experiencing the coupled energy, is required in order to reduce the effect(s) of the coupled energy.

Coupled signal/energy on a portion of the implantable system 100 may cause a resonant effect, which could cause adverse conditions, such as heating of the leads. Therefore, it may be desirable to reduce the resonant effects of a coupled signal/energy. In order to create an anti-resonant effect, a reduction of heating, or to counter other adverse effects resulting from the coupled signal/energy, a look-up process may be performed by the IMD 200. Data relating to the characteristic(s) (e.g., frequency, amplitude, etc.,) of the coupled energy may be used to look up a counter-coupling impedance that would reduce the adverse effect(s) of the coupled signal/energy. This impedance may reduce the magnitude of the coupled energy. The IMD 200 may look up impedance data relating to the detected frequency of the coupled energy, find or determine a corresponding impedance that may reduce the effect of the detected frequency, and implement such impedance.

The signal detection unit 240 may also comprise a bandpass filter circuit 320. The bandpass filter circuit may comprise various filters, such as a highpass filter 325 and/or a lowpass filter 327. These filters may filter out various frequency ranges so that the coupled signal/energy may be analyzed. This analysis may be used to determine the type of impedance adjustment or response that may be desirable. For example, the bandpass filter 320 may perform filtering processes to detect the presence of a 1.5 Tesla and/or a 3.0 Tesla Magnetic Resonance Imaging (MRI) signal/energy. Other types of MRI signals may also be detected by the IMD 200 using the bandpass filter circuit 320.

Further, the signal detection unit 240 may also comprise envelope comparator circuitry 330. The envelope comparator circuitry 330 may provide comparison of the coupled energy/signal in a range of values to reference-voltage or reference-current signals in order to characterize the coupled energy. Further, the signal detection unit 240 may also comprise a signal threshold detector 340 that is capable of detecting a voltage or current level threshold relating to the coupled signal or energy. Additionally, other sensors, such as thermal sensors 350, may be encompassed within the signal detection unit 240. The thermal sensor 350, for example, may detect the thermal energy on the leads that may be caused by coupled energy.

Based upon the various indications provided by the various units in the signal detection unit 240, or based upon program signals from, e.g., an external unit 270 under the control of a healthcare provider, one or more impedance adjustment actions may be initiated by the IMD 200. The IMD 200 may use data provided by the signal detection unit 240 to perform a calculation of the impedance that may be used to counter the detected energy. This calculation may include performing a look-up function in a look-up table that may be stored in the memory unit 217. Those skilled in the art having benefit of the present disclosure will appreciate that other forms of signal detection may be performed and still remain within the spirit and scope of the present invention.

Figure 4:
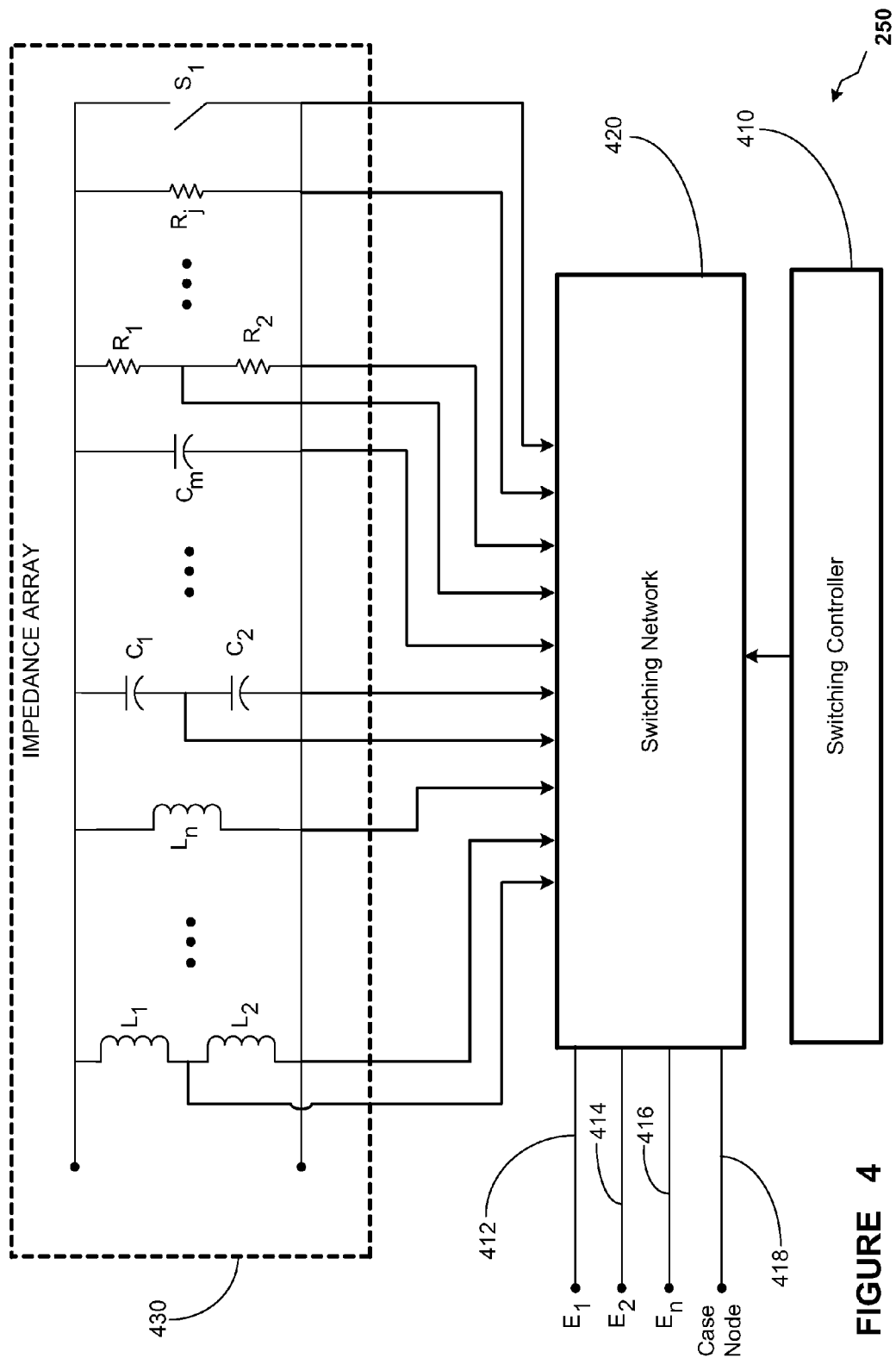
FIG. 4 is a more detailed stylized depiction of an impedance unit of the implantable medical device of FIG. 2, in accordance with one illustrative embodiment of the present invention.

Turning now to FIG. 4, a stylized depiction of the impedance unit 250 is provided, in accordance with an illustrative embodiment of the present invention. The impedance unit 250 may comprise a switching controller 410, a switching network 420, and an impedance array 430. The switching controller 410 may comprise hardware, software, and/or firmware units that are capable of controlling the switching of various impedance values associated with various portions of the implantable system 100. The switching controller 410, along with the switching network 420, which may comprise a plurality of switches 420, may be used to switch various portions of the impedance array 430.

The impedance array 430 may comprise a plurality of inductive, capacitive, resistive, and/or active components, as well as a simple open or short circuit. As illustrated in FIG. 4, the impedance array 430 may comprise an inductive impedance $L_1$ in series with another inductive impedance $L_2$. The combination of the series inductive impedances $L_1$ and $L_2$ may be arranged in parallel with a plurality of inductive impedances, such as $L_n$. These inductive impedances may be arranged in parallel with a set of capacitive impedances $C_1$, and $C_2$, which are arranged in series. The series capacitors $C_1$ and $C_2$ may be arranged in parallel with a plurality of parallel capacitive impedances, such as $C_m$. Similarly, these capacitive elements may be arranged parallel related to a pair of series resistors $R_1$, $R_2$, which may be arranged in parallel with various parallel resistors, such as $R_j$. Also, a fixed or switchable open or short-circuit, $S_1$, may be used alone, or in combination with the impedances described above, wherein the short-circuit may also be switched on or off by the switching network 420.

In addition to purely passive impedances, active circuitry of adequate frequency response capability may be employed to actively reduce or substantially cancel coupled energy. Referring again to FIG. 2, the IMD 200 may comprise an active cancellation unit 257 that is capable of providing an active signal to reduce coupled energy. For example, the active cancellation unit 257 is capable of providing a controlled current signal that may be used to reduce coupled energy. The active cancellation unit 257 may provide a current signal to cause the equivalent current induced by the energy to become substantially zero. The output of the active cancellation unit 257 may be set to provide a 0 Amp current in the presence of the coupled energy/signal. The active cancellation unit 257 may comprise one or more controlled current supply circuits. In one embodiment, the active cancellation unit 257 may provide a current signal that is capable of substantially canceling a current that is induced by the coupled energy/signal. Although illustrated in FIG. 2 as distinct from impedance unit 250, it will be appreciated that the active cancellation unit may comprise a portion of impedance unit 250.

Referring again to FIG. 4, the switching network 420 is capable of switching various portions of the components of the impedance array 430 in relation to various points of the IMD 200. These points may include nodes that are coupled to the switching network, such as a node from a first electrode $E_1$, on a line 412; a node from a second electrode $E_2$, on a line 414; a node from an $n^{th}$ electrode $E_n$, on a line 416; and a case node 418 representing the case associated with the IMD 200. The lines 412, 414, and 416 may represent leads. Any number of impedances may be selected and switched by the switching network 420 to provide a desired impedance in relation to two points between any one of the nodes 412, 414, 416 and/or 418. Therefore, based upon the type of signal/energy that is detected by the signal detection unit 240, or determined in advance by, e.g., a physician prior to conducting an MRI diagnostic procedure on a patient having an implanted medical device 200, the switching controller 410 may prompt the switching network 420 to provide a particular impedance in relation to any portion of the implantable system 100 where the coupled energy/signal is detected or determined in advance. This impedance may be selected by invoking any combination of the components of the impedance array 430.

The impedance selected from the impedance array 430 is switched such that the amplitude, frequency, and/or other characteristics of the coupled signal/energy may be brought within an acceptable level. In other words, the presence of the coupled signal/energy is reduced by selecting particular impedances and switching them on or off between any two of the nodes described above. For example, the impedance array 430 may be manipulated such that if a 1.5 Tesla MRI energy is detected in a portion of the implantable system 100 (e.g., a lead), the impedance associated with that portion may be adjusted to provide for minimal radio frequency (RF) induced heating at 64 MHz. As another example, the impedance array 430 may be manipulated such that if a 3.0 Tesla MRI energy is detected in a portion of the implantable system 100 (e.g., a lead), the impedance associated with that portion may be adjusted to provide for minimal RF induced heating at 128 MHz.

Figure 5:
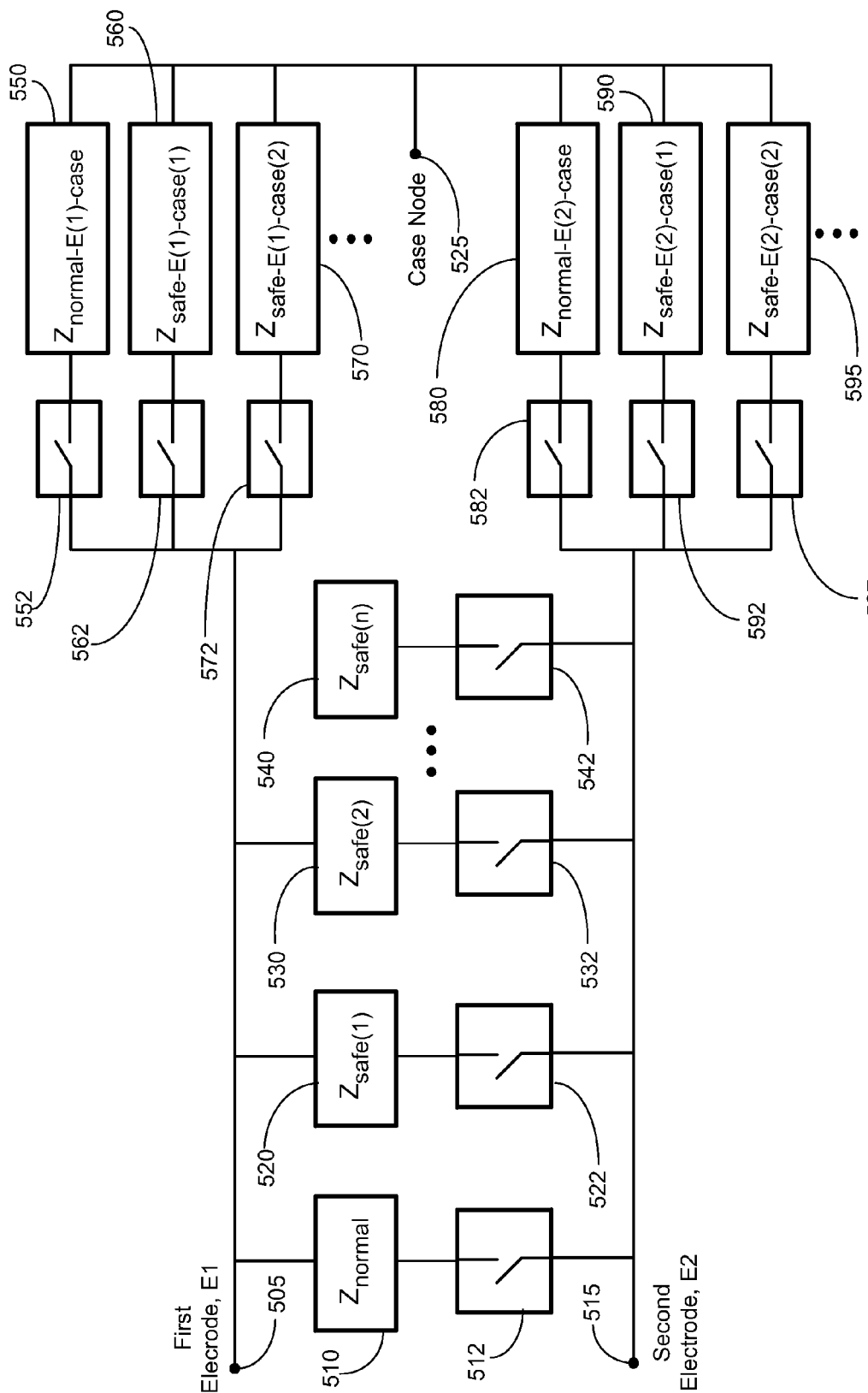
FIG. 5 is a stylized depiction of a schematic relating to various impedances between various points of an implantable medical device system, in accordance with one illustrative embodiment of the present invention.

Turning now to FIG. 5, a schematic relating to a representative impedance layout associated with an illustrative embodiment of the present invention is provided. For the purposes of clarity of description, only nodes associated with a first electrode 505 and a second electrode 515, along with a node associated with the casing of the IMD 200 (node 525), are described. However, those skilled in the art having benefit of the present disclosure would appreciate that the schematics may include various other connections between various other nodes and remain within the spirit and scope of the present invention.

A set of impedances may be predetermined and may be switched on or off between various points, as illustrated in FIG. 5. For example, during normal operation, a normal impedance $Z_{normal}$ 510 may be present between the nodes and/or leads associated with the first and second electrodes 505, 515. The node 505 may represent the lead that connects the first electrode to the IMD 200. The node 515 may represent the lead that connects the second electrode to the IMD 200. Together, the leads/nodes 505 and 515 may form a lead set. A switch 512 may be controlled such that during normal operations of the IMD 200, the switch 512 is closed to provide the normal impedance, $Z_{normal}$ 510. The normal impedance $Z_{normal}$ 510 may be predetermined to provide for desirable efficiency in delivering the stimulation signal from the IMD 200. However, upon detection of a significant amount of coupled signal/energy on the node 505 or 515, or upon receiving a signal from a healthcare provided indicating that a coupled signal may be provided in the future, one of a plurality of impedances that may be desirable for a safe-mode operation may be switched on, while the $Z_{normal}$ 510 is switched off. This impedance change may be implemented such that normal operation of the IMD 200 may continue in a safe mode, or be suspended, until the presence of the coupled energy is substantially depleted or a signal is received instructing the IMD 200 that a known coupled signal/energy has been removed and that normal operation should resume. The safe mode may represent a mode of operation of the IMD 200 where the impedance relating to the portion of the IMD 200 that is affected by a coupled signal/energy may be modified such that the effect(s) of the coupled signal/energy are reduced.

During the safe mode operation of the IMD 200, a number of impedances, $Z_{safe(1)}$ 520, $Z_{safe(2)}$ 530, through $Z_{safe(n)}$ 540 may be selected to provide for the attenuation of the coupled signal/energy. Each of these impedances may be respectively switched on or off in any combination by the switches 522, 532, 542. The normal impedance $Z_{normal}$ 510 may be invoked or disabled by the switch 512.

As an example, for a particular coupled signal/energy that is detected (e.g., energy from a 1.5 Tesla MRI signal), it may be determined that $Z_{safe(1)}$ 520 is an appropriate response to substantially reduce the effect(s) of the coupled energy. For example, the $Z_{safe(1)}$ 520 may provide for a reduction of RF heating at 64 MHz. As another example, for a particular coupled signal/energy that is detected (e.g., energy from a 3.0 Tesla MRI signal), it may be determined that $Z_{safe(2)}$ 530 is an appropriate response to substantially reduce the effect of the coupled energy. For instance, the $Z_{safe(2)}$ 530 may provide for a reduction of RF heating at 128 MHz. Therefore, upon such a detection, or an external input indicating that such a signal is expected to occur in the near future, the impedance $Z_{normal}$ 510 may be switched off by the switch 512, while the impedance $Z_{safe(2)}$ may be switched on by the switch 532. Hence, during the presence of the particular coupled energy, a safe impedance $Z_{safe(2)}$ 530 is implemented between the nodes associated with the first electrode 505 and the second electrode 515. The term "safe impedance" refers to an impedance that may reduce the affects of a coupled energy. Upon termination of the event that caused the coupled energy, the $Z_{safe(2)}$ impedance 530 may be switched off, and the $Z_{normal}$ 510 impedance may be switched on by the switch 512. Hence, after the presence of the coupled energy is substantially diminished, normal operations of the IMD 200 may be resumed.

Similarly, the impedance between other nodes of the implantable system 100 may also be controlled. For example, the impedance between the node 505 associated with the first electrode 505 and case associated with the IMD 200 on the node 525, may be altered by switching from a normal first-electrode-to-case impedance, $Z_{normal-E1-case}$ 550, to another impedance. The normal first-electrode-to-case impedance, $Z_{normal-E1-case}$ 550 may represent the normal impedance that is to be implemented between the node 505 of the first electrode 505, and the node associated with the case 525. Upon the detection of a coupled signal/energy between these two nodes, or on receiving a signal indicating that the impending presence of a known coupled signal/energy, the IMD 200 may switch the impedance $Z_{normal-E1-case(1)}$ 550 off and may implement another safe mode impedance, such as the impedance $Z_{safe-E1-case(1)}$ 560, or the impedance $Z_{safe-E1-case(2)}$ 570. This switching may be controlled by the switches 552, 562, and/or 572. Therefore, upon detection of the presence of a particular coupled signal/energy, such as an MRI signal, the $Z_{safe-E-case(1)}$ 560 may be switched on by the switch 562 to reduce the coupled energy experienced by a portion of the implantable system 100.

Similarly, the impedance between the node 515 associated with a second electrode, and the node 525 associated with the case may be modified based upon a coupled signal/energy detected on at least one of these two nodes. The normal impedance $Z_{normal-E2-case}$ 580 is the normal impedance used during normal operation of the IMD 200. The normal impedance $Z_{normal-E2-case}$ 580 may be switched on or off by the switch 582. Upon detection of a coupled signal/energy, the IMD 200 may switch on the $Z_{safe-E2-case(1)}$ and/or the $Z_{safe-E2-case(2)}$ by switching one or more of the switches 582, 592 and/or 597. Therefore, as illustrated in FIG. 5, various impedances between various nodes associated with the IMD and surrounding components of the implantable system 100 may be implemented. Those skilled in the art would appreciate that the blocks represented by the impedances described above may comprise the impedance array 430 of FIG. 4 in one embodiment. In an alternative embodiment, the impedance blocks of FIG. 5 may comprise a predetermined set of impedances.

Figure 6:
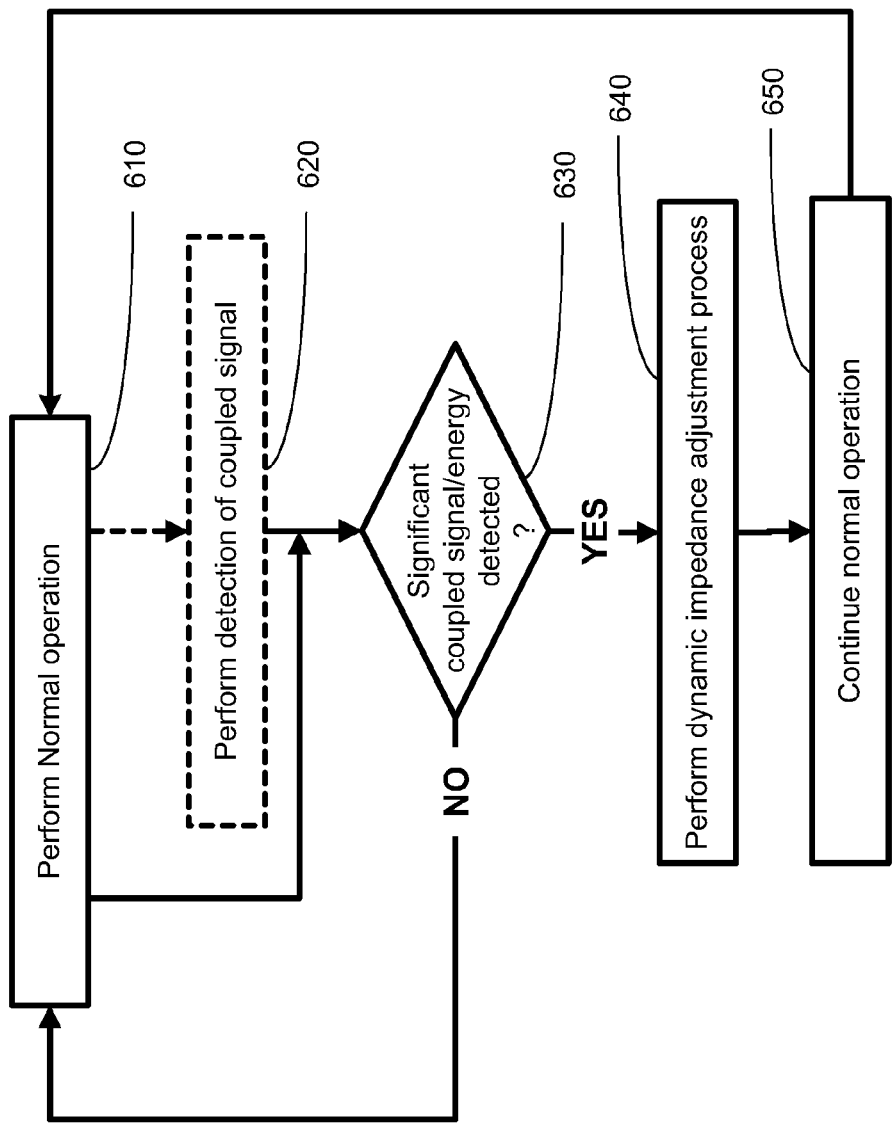
FIG. 6 illustrates a flowchart depiction of a method, in accordance with multiple illustrative embodiments of the present invention.

Turning now to FIG. 6, a flowchart associated with a method in accordance with multiple embodiments of the present invention is provided. The IMD 200 may perform normal operations (block 610) until a significant amount of coupled signal/energy is detected. In one embodiment, the IMD 200 may perform a dynamic impedance adjustment process (block 640). The dynamic impedance adjustment process may call for implementing a safe mode operation of the IMD 200. The safe mode operation may comprise delivering stimulation while a modified impedance is implemented. The safe mode operation may also, or alternatively, involve implementing an active cancellation of the energy, which may be performed by the active cancellation unit 257. The safe mode may also involve suspending or reducing the delivery of therapy by the IMD 200. The safe mode implementation may be initiated by a variety of methods, such as operator input, external input, input by the patient, and the like.

FIG. 6 also illustrates an alternative embodiment path denoted by dotted lines and dotted blocks. The alternative embodiment may call for performing a detection of a signal/energy to initiate an implementation of the safe-mode. In this alternative embodiment, the IMD 200 may perform a detection operation to detect if a coupled signal has been coupled to any portion of the implantable system 100 (block 620). For example, the IMD 200 may perform a detection algorithm to detect the presence or absence of coupled energy in the leads connected to the IMD 200. The detection step 620 may be an ongoing or a periodic function that may be predetermined or may be adjusted using external inputs. A number of types of detecting methods may be employed, including signal detection methods, comparison methods, thermal energy sensing methods, etc.

The IMD 200 may then make a determination whether significant coupled signal/energy is detected (block 630). In other words, the coupled energy that is detected may be analyzed (e.g., a comparison to a predetermined threshold) to determine whether the coupled energy should be addressed. If significant coupled energy is not detected, the IMD may continue to perform normal operations, which may include further continuous or periodic detection steps to check for the presence/absence of coupled energy.

Upon a determination that significant coupled signal/energy has been detected, the IMD may perform a dynamic impedance adjustment process (block 640). A more detailed description of the dynamic impedance adjustment process of block 640, is provided in FIG. 7 and the accompanying description below. Upon performing the dynamic impedance adjustment process, the IMD 200 may continue normal operations (block 650). Therefore, the IMD 200 may continue detecting any coupled signal/energy and the process may be repeated.

Figure 7:
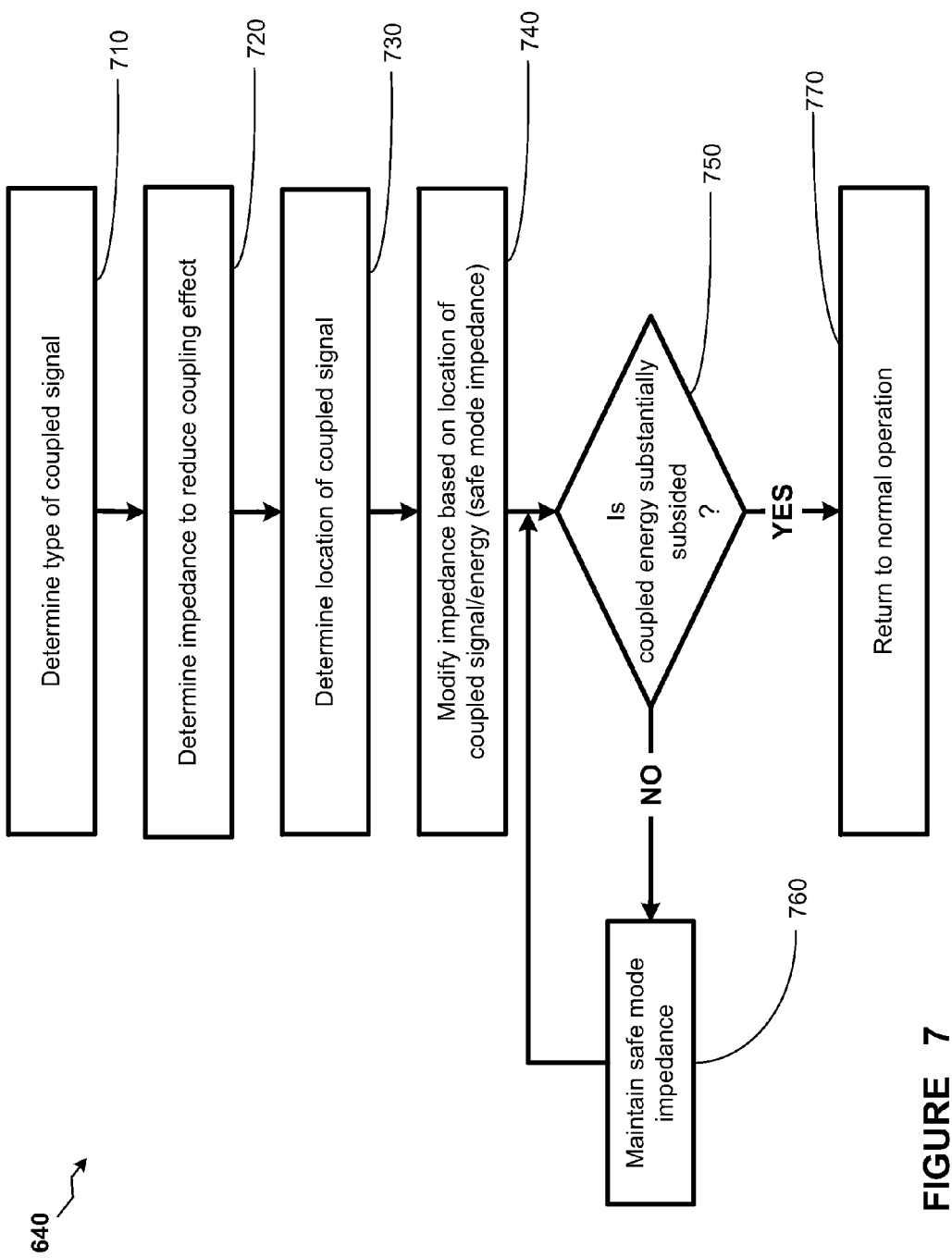
FIG. 7 illustrates a more detailed flowchart depiction of performing a dynamic impedance adjustment process of FIG. 6, in accordance with one illustrative embodiment of the present invention.

Turning now to FIG. 7, a more detailed flowchart depiction of the steps associated with performing the dynamic impedance adjustment process of block 640 in FIG. 6 is illustrated. Upon a determination that a significant amount of coupled signal/energy is coupled to a portion of the IMD 200, the IMD 200 may identify the type of coupled signal/energy (block 710). For example, a certain MRI signal with a particular frequency and/or amplitude (e.g., 0.3 Tesla MRI signal, 0.5 Tesla MRI signal, 0.7 Tesla MRI signal, 1.0 Tesla MRI signal, a 1.5 Tesla MRI signal, a 3.0 Tesla MRI signal, a 5.0 Tesla MRI signal, a 7.0 Tesla MRI signal, or the like) may be identified as the coupled energy on a portion (e.g., a lead) of the implantable system 100. Other characterizations of the signals may be performed to identify the characteristics of the coupled energy/signal or noise.

Upon a determination of the type of coupled energy that is detected, a determination may be made as to the type of impedance that is to be implemented to reduce the coupling effect (block 720). This may include performing a look-up from a look-up table to identify a particular impedance that is to be implemented. Other input, such as manual input, or input from the external device 270, may be received in order to determine the impedance that would cause a reduction in the coupled energy.

The IMD 200 may also then determine the location of the coupled signal 730 in order to implement the impedance (block 730). In other words, the IMD 200 may determine the safe mode impedance between a particular set of nodes to switch on or off. The safe mode may relate to continued operation and delivery of stimulation in predetermined intervals, albeit during a configuration where the impedance is altered. Upon determination of the location of the coupled signal, the impedance may be modified based on the location of the coupled signal/energy (block 740). For example, the impedance between a first electrode and a node associated with the case of the IMD may be modified based on detecting a coupled signal/energy on the lead associated with the first electrode. Based upon the modification, a determination is made if the coupled signal/energy has substantially subsided (block 750). This may be determined by an indication that a particular signal source has been turned off. This indication may also be provided by an external indication, e.g., by a physician using an external programmer unit such as external unit 270 to indicate that a particular MRI procedure has been completed. The subsiding of the coupled signal/energy may also be determined by detecting that the coupled energy has substantially subsided, i.e., by a detecting step similar to step 620 and subsequent determination step similar to step 630 that no significant coupled signal/energy is present. If a determination is made that the coupled energy has not substantially subsided, the safe mode impedance is maintained (block 760). However, if the coupled energy or the event that causes such a coupled energy has subsided, then the impedances may be switched back to normal (block 770). Therefore, the safe mode is then terminated and a normal mode is initiated and the normal operation of the IMD 200 is resumed.

Utilizing the embodiments of the present invention, coupled signal/energy may be substantially attenuated. This attenuation may be achieved by using one of a number of various impedances between various portion(s) of the implantable system 100. Utilizing the dynamic impedance adjustment of the present invention, a dynamic safe mode adjustment may be implemented to reduce the effects of coupled energy. For example, if a patient implanted with an IMD 200 enters an MRI chamber, the safe mode may be implemented until the MRI signals have been turned off to prevent adverse effects caused by the coupling of the MRI energy. Utilizing the embodiments of the present invention, a dynamic response to coupled signal/energy may be performed to promote a safer and more accurate operation of implantable medical devices. Embodiments of the present invention may be implemented for a variety of types of implantable devices that are capable of stimulating any portion of the human body.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. A method for minimizing current in a lead circuit of an implantable medical device (IMD) system induced by coupled energy from an external source, comprising:
providing a first impedance between a first node and a second node of the IMD, the lead circuit comprising a first lead configured to couple the first node of the IMD to a first target tissue and a second lead configured to couple the second node of the IMD to a second target tissue;
receiving an indication of the presence of the coupled energy on the lead circuit;
determining a characteristic of the coupled energy;
selecting a second impedance from a plurality of impedances based at least in part on the characteristic of the coupled energy, the second impedance selected to minimize the current induced by the coupled energy; and
providing the selected second impedance between the first node and the second node in place of the first impedance, wherein the first impedance and the second impedance are not open circuit impedances.

2. The method of claim 1, further comprising:
providing a stimulation signal from the IMD through the lead circuit to deliver a therapy in the presence of the coupled energy, the IMD having the second impedance between the first node and the second node.

3. The method of claim 2, wherein the stimulation signal is provided to a vagus nerve.

4. The method of claim 1, further comprising:
determining that the coupled energy between the first node and the second node has substantially diminished; and
providing the first impedance in place of the second impedance between the first node and the second node based upon determining that the coupled energy on the lead circuit has substantially diminished.

5. The method of claim 1, wherein the characteristic of the coupled energy comprises a magnetic resonance imaging (MRI) signal level including one of 0.3 Tesla, 0.5 Tesla, 0.7 Tesla, 1.0 Tesla, 1.5 Tesla, 3.0 Tesla, 5.0 Tesla, and 7.0 Tesla.

6. The method of claim 1, wherein the second impedance is selected to substantially reduce radio frequency (RF) heating of the lead circuit at one of about 128 MHz, about 64 MHz, and about 42.67 MHz.

7. The method of claim 1, wherein the second impedance includes at least one of a capacitor and an inductor.

8. The method of claim 1, wherein receiving the indication of the presence of the coupled energy comprises receiving at least one of an input from a source external to the IMD and a signal responsive to a detection of the coupled energy.

9. The method of claim 1, further comprising:
determining that the coupled energy on the lead circuit has changed to a second coupled energy;
determining a second characteristic of the second coupled energy;
selecting a third impedance from the plurality of impedances based at least in part on the second characteristic of the second coupled energy, the third impedance selected to minimize current induced by the second coupled energy; and
providing the selected third impedance between the first node and the second node in place of the second impedance, wherein the third impedance is not an open circuit impedance.

10. The method of claim 1, wherein determining the characteristic of the coupled energy comprises determining that the coupled energy is greater than a predetermined threshold.

11. The method of claim 1, wherein determining the characteristic of the coupled energy comprises determining a frequency of the coupled energy.

12. The method of claim 11, wherein the second impedance is selected based at least in part on the frequency of the coupled energy.

13. The method of claim 1, wherein the plurality of impedances are provided by a programmable impedance array between the first node and the second node.

14. A method for minimizing current in a lead circuit of an implantable medical device (IMD) system induced by coupled energy from an external source, comprising:
providing a first impedance between a first node and a second node of the IMD, the lead circuit comprising a first lead configured to coupled the first node of the IMD to a first portion of a cranial nerve and a second lead configured to couple the second node of the IMD to a second portion of the cranial nerve;
detecting the coupled energy on the lead circuit at a detection unit of the IMD;
determining a characteristic of the coupled energy at the detection unit;
selecting a second impedance from at least three impedances based at least in part on the characteristic of the coupled energy, the second impedance selected to minimize the current induced by the coupled energy;
providing the selected second impedance between the first node and the second node in place of the first impedance, wherein the first impedance and the second impedance are not open circuit impedances; and
providing a stimulation signal from the IMD through the lead circuit to deliver a therapy to the cranial nerve in the presence of the coupled energy, the IMD having the second impedance between the first node and the second node.

15. The method of claim 14, wherein the cranial nerve is a vagus nerve.

16. The method of claim 14, further comprising:
determining that the coupled energy between the first node and the second node has substantially diminished; and
providing the first impedance in place of the second impedance between the first node and the second node based upon determining that the coupled energy on the lead circuit has substantially diminished.

17. The method of claim 14, wherein the characteristic of the coupled energy comprises a magnetic resonance imaging (MRI) signal level including one of 0.3 Tesla, 0.5 Tesla, 0.7 Tesla, 1.0 Tesla, 1.5 Tesla, 3.0 Tesla, 5.0 Tesla, and 7.0 Tesla.

18. The method of claim 14, wherein the second impedance is selected to substantially reduce radio frequency (RF) heating of the lead circuit at one of about 128 MHz, about 64 MHz, and about 42.67 MHz.

19. The method of claim 14, wherein the second impedance includes at least one of a capacitor and an inductor.

20. The method of claim 14, further comprising:
   determining that the coupled energy on the lead circuit has changed to a second coupled energy;
   determining a second characteristic of the second coupled energy;
   selecting a third impedance from the plurality of impedances based at least in part on the second characteristic of the second coupled energy, the third impedance selected to minimize current induced by the second coupled energy; and
   providing the selected third impedance between the first node and the second node in place of the second impedance, wherein the third impedance is not an open circuit impedance.

21. The method of claim 14, wherein determining the characteristic of the coupled energy comprises at least one of determining that the coupled energy is greater than a predetermined threshold and determining the characteristic of the coupled energy comprises determining a frequency of the coupled energy.

22. The method of claim 14, wherein the at least three impedances are provided by a programmable impedance array between the first node and the second node.

23. A method for minimizing current in a lead circuit of an implantable medical device (IMD) system induced by coupled energy from an external source, comprising:
   providing a first impedance between a first node and a second node of the IMD, the lead circuit comprising a first lead configured to coupled the first node of the IMD to a first portion of a cranial nerve and a second lead configured to couple the second node of the IMD to a second portion of the cranial nerve;
   detecting the coupled energy on the lead circuit at a detection unit of the IMD;
   determining a characteristic of the coupled energy at the detection unit;
   selecting a second impedance from at least three impedances in a programmable impedance array based at least in part on the characteristic of the coupled energy, the second impedance selected to minimize the current induced by the coupled energy;
   providing the selected second impedance between the first node and the second node in place of the first impedance, wherein the first impedance and the second impedance are not open circuit impedances;
   providing a stimulation signal from the IMD through the lead circuit to deliver a therapy to the cranial nerve in the presence of the coupled energy, the IMD having the second impedance between the first node and the second node;
   determining that the coupled energy on the lead circuit has changed to a second coupled energy; and
   dynamically adjusting the second impedance to minimize a second current induced by the second coupled energy.

24. The method of claim 23, wherein the second impedance includes at least one of a capacitor and an inductor.

25. The method of claim 23, wherein the second impedance is selected to substantially reduce radio frequency (RF) heating of the lead circuit at one of about 128 MHz, about 64 MHz, and about 42.67 MHz.

* * * * *